(12) United States Patent  
Muller et al.

(10) Patent No.: US 6,974,458 B2
(45) Date of Patent: Dec. 13, 2005

(54) MEDICAL DEVICE WITH IMPROVED POWER PLUG CONNECTION

(75) Inventors: Richard P. Muller, Bronx, NY (US); Murray Beaver, Stamford, CT (US); Ezra Navok, Stamford, CT (US)

(73) Assignee: ACMI Corporation, Southborough, MA (US)

( * ) Notice: Subject to any disclaimer, the term of this patent is extended or adjusted under 35 U.S.C. 154(b) by 129 days.

(21) Appl. No.: 10/411,774

(22) Filed: Apr. 11, 2003

(65) Prior Publication Data

US 2003/0195512 A1 Oct. 16, 2003

Related U.S. Application Data

(60) Provisional application No. 60/372,097, filed on Apr. 12, 2002.

(51) Int. Cl.[7] ............................................. A61B 18/18
(52) U.S. Cl. ..................... 606/46; 439/224; 439/481; 439/732; 606/32

(58) Field of Search ..................... 606/32–52; 439/224, 439/481, 271, 909

(56) References Cited

U.S. PATENT DOCUMENTS

| 4,149,538 A | 4/1979 | Mrava et al. |
| 4,538,610 A | 9/1985 | Kubota |
| 4,917,621 A * | 4/1990 | Grossi et al. ................ 439/224 |
| 6,322,494 B1 * | 11/2001 | Bullivant et al. ........... 600/104 |

* cited by examiner

Primary Examiner—Beverly M. Flanagan
Assistant Examiner—Matthew J. Kasztejna
(74) Attorney, Agent, or Firm—Ganz Law, P.C.

(57) ABSTRACT

A bipolar endoscopic device is provided having a detachable power cord with a plug capable of forming a sealed connection with the endoscopic device. The plug is connected at a back face of a movable guide member of the endoscopic device and can be oriented in different orientations to accommodate different operators. The detachable plug forms a sealed connection with the endoscopic device so that the electrosurgical connection cannot be short-circuited by the outside environment such as a saline irrigation fluid.

26 Claims, 4 Drawing Sheets

MEDICAL DEVICE WITH IMPROVED POWER PLUG CONNECTION

This invention claims the benefit of co-pending U.S. Provisional Application No. 60/372,097, entitled "Medical Device With Improved Power Plug Connection", filed Apr. 12, 2002, the entire disclosure of which is hereby incorporated by reference as if set forth in its entirety for all purposes.

FIELD OF THE INVENTION

This invention relates to electrosurgical instruments and, more particularly, to endoscopes with an improved power plug connection for associated bi-polar electrode assemblies.

BACKGROUND OF THE INVENTION

While the inventive principles of the present invention are applicable to a variety of electrosurgical instruments, as a person skilled in the art will readily appreciate, for purposes of illustration and not limitation, the present invention will be described in reference to one possible embodiment, namely a resectoscope.

Generally, resectoscopes comprise a hollow sheath, a working element, a telescope and an electrode. The working element generally has a guide block that can slide or move, such as by a rack and pinion mechanism or spring, to move the electrode relative to the telescope. The guide block generally has a hole or connector for receiving a portion of the electrode and another hole for receiving an electric plug. The electric plug supplies electricity to the electrode for resection or the like. U.S. Pat. No. 4,538,610 to Kubota shows one type of resectoscope having a guide block or movable member and an extending connecting part. U.S. Pat. No. 4,149,538 to Mrava et al shows a resectoscope having a slide portion with a receptacle or channel for receiving the plug of an electrical lead (not shown). However, problems exist with these and other prior art devices.

There are generally two types of instruments used in electrosurgery. Monopolar devices employ a single electrode at the operative end of the instrument and an electrode return plate generally located under and in contact with the patient. The electrode plate constitutes a second dispersive electrode so that electrical current used to ablate or alter tissue passes through the patient.

Bipolar devices employ two electrodes spaced closely together at the operative end of the instrument so that the flow of current is confined to the tissue in close proximity to the electrodes. Bipolar devices require a saline or other electrolytic environment in order to provide a conductive path between the electrodes. One problem with bipolar devices is that the electrical connections must be electrically isolated from the saline environment in order to prevent electrical short-circuiting. Short-circuiting will reduce the effectiveness of the resectoscope for its intended function. In particular, the electric plug or bipolar cord must be sealingly engaged with the device. In order to provide a sealed connection prior art bipolar devices have integrated the bipolar cord into the device as a single unit. However, such an integrated design presents difficulties in maintaining a seal between the electrode and working element that is both leak proof and of low frictional drag on the electrode when it is mechanically moved in and out of the sheath by the user.

During an operation on a patient, the doctor or operator must feel confident and secure with his instrument. In the past, various different manufacturers of medical instruments produced different designs of instruments having electric cords connected at various different locations on their individual instruments. Doctors who have developed a preference for a certain type of instrument may feel uncomfortable in changing to other types or makes of the same instrument merely because of the change in orientation of the electrical wire such as in a resectoscope. Thus, a user who is comfortable with a resectoscope having a connector located on the top of the resectoscope such as that shown, for example, in Kubota ('610), might feel uncomfortable using a resectoscope in which the electric power cord extends downward rather than upward such as shown, for example, in Mrava et al ('538). In addition, the resectoscope shown and described in Mrava et al ('538) would probably be uncomfortable for a left handed user.

U.S. Pat. No. 4,917,621 to Grossi et al, the subject matter of which is herein incorporated by reference, discloses a resectoscope having a disconnectable electrical plug that can be connected to the device on either a first or a second side. However, the electrical plug does not sealingly mate with the device. Accordingly, there is a need for a medical instrument having a power cord system that is adaptable to accommodate different user preferences.

In addition, there is a need for improved disposable active cords that are convenient to use and that provide more optimal sealing to protect against short-circuiting.

SUMMARY OF THE INVENTION

The foregoing problems are overcome and other advantages are provided by a medical endoscope with an improved electrical plug receptacle and electrical plug connector and power cord assembly.

It is therefore an object of the present invention to provide a detachable active power cord for a bipolar endoscopic device having a plug connector capable of forming a sealed connection with the electrode device.

It is another object of the present invention to provide a detachable power cord for use with a bipolar endoscopic device that can be connected to the device in different orientations to accommodate different operators.

It is a further object of the present invention to provide a detachable power cord or a bipolar device for use in a saline environment.

Still another object of the present invention is to provide a power cord for a bipolar endoscopic device that is interchangeable with various bipolar electrode models.

In one of many possible embodiments, the present invention contemplates an endoscope including a frame and a guide block, the guide block having an electrical plug recess located on a back face of the guide block. The recess extends through the guide block and intersects an opening for an electrode such that an electrical connector can be directly connected to the electrode assembly. The electrical connector can be inserted into the guide block so that the power cord extends from either side of the guide block to accommodate either a left or right handed operator.

The electrical connector is made of non-conductive material such as, for example, natural or synthetic rubber and preferably has a tapered shape to allow the user to more easily matingly engage the electrical connector into the opening in the guide block.

The foregoing aspects and other features of the invention are explained in the following description, taken in connection with the accompanying drawings.

DETAILED DESCRIPTION OF THE INVENTION

Figure 1:
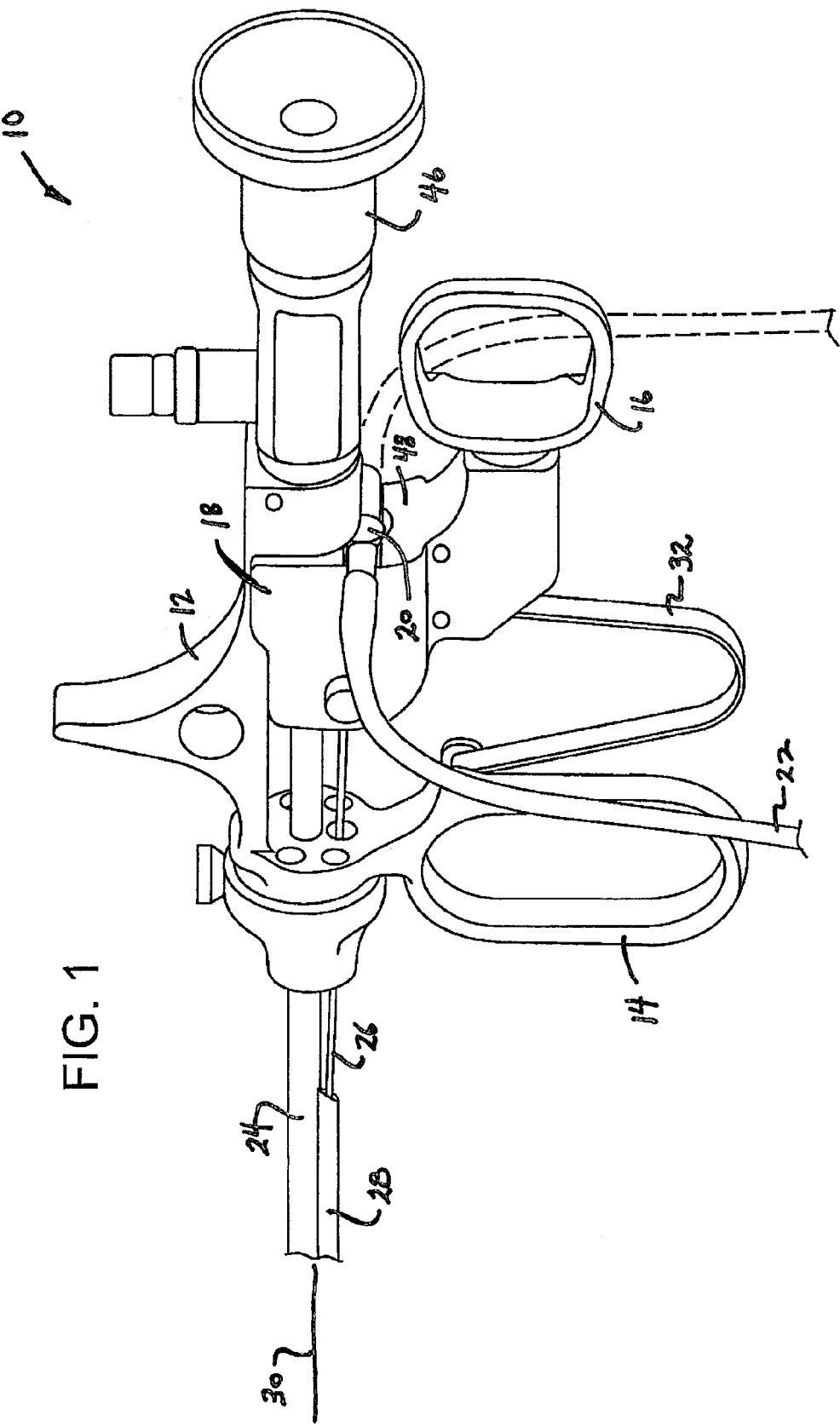
FIG. 1 is a perspective rear view of the handle section of an electrosurgical instrument with a detachable power cord incorporating features of the invention shown attached to the electrosurgical instrument.
Figure 2:
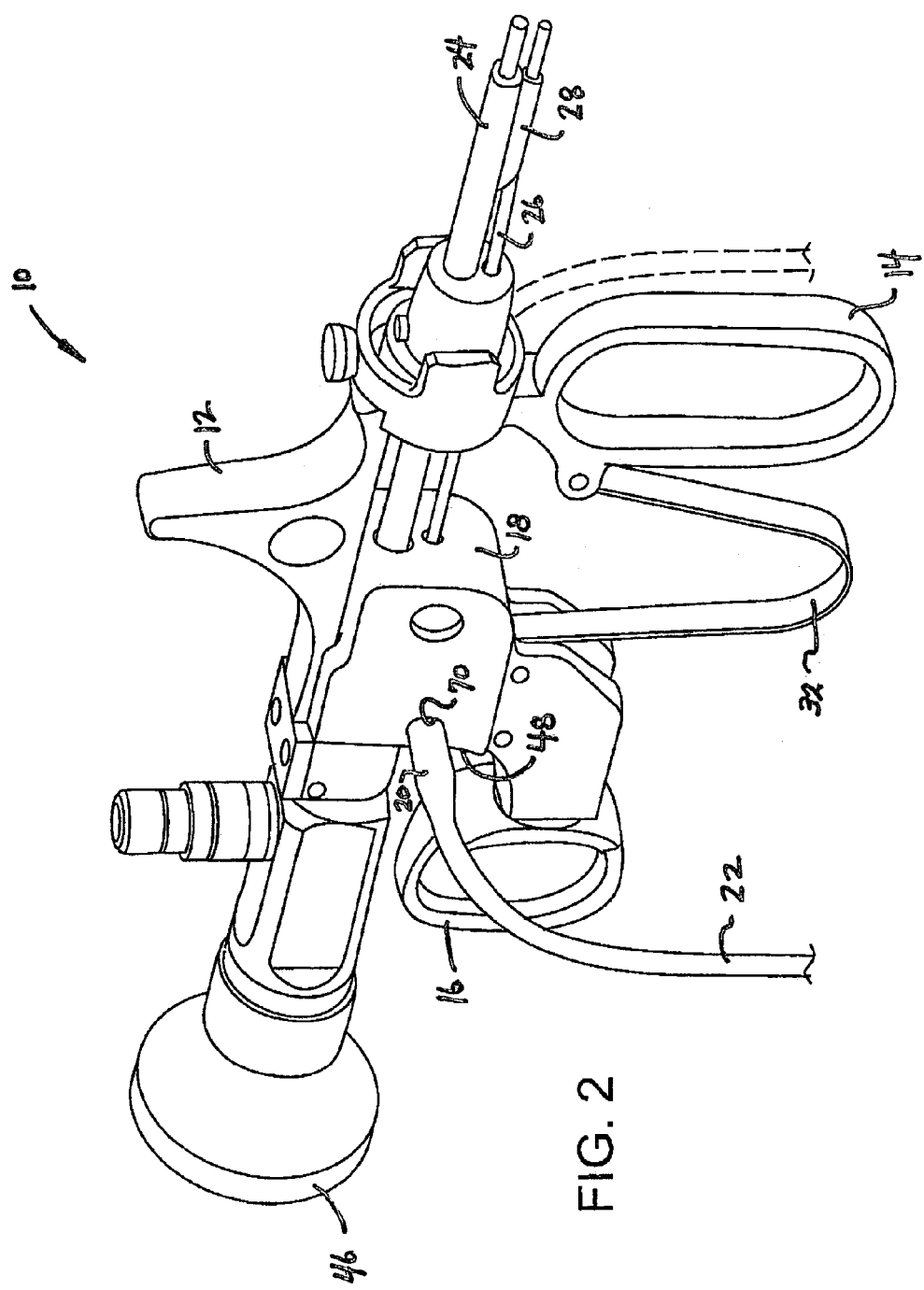
FIG. 2 is a perspective front view of the handle section shown in FIG. 1 with the power cord shown attached in an alternative position.

FIGS. 1 and 2 show partial perspective views of the handle section of a resectoscope working element 10. Although the present invention will be described with reference to the working element 10 of FIGS. 1–6, it should be understood that the present invention may be used with various different types of resectoscope working elements, including Iglesias type working elements and McCarthy type working elements. The present invention may also be employed in any type of medical endoscope using an electrode but is particularly suited to bipolar devices used with an electrolytic irrigating fluid such as normal saline. In addition, it should be understood that the elements of the present invention may have any suitable size, shape or type of material.

Figure 3:
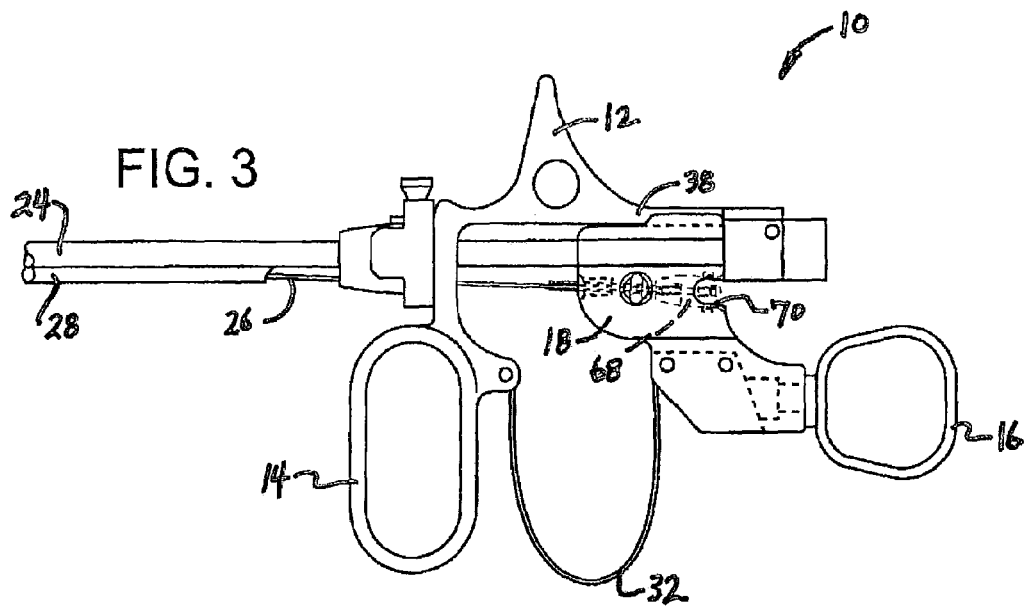
FIG. 3 is a partial side view of the handle section shown in FIG. 1.
Figure 4:
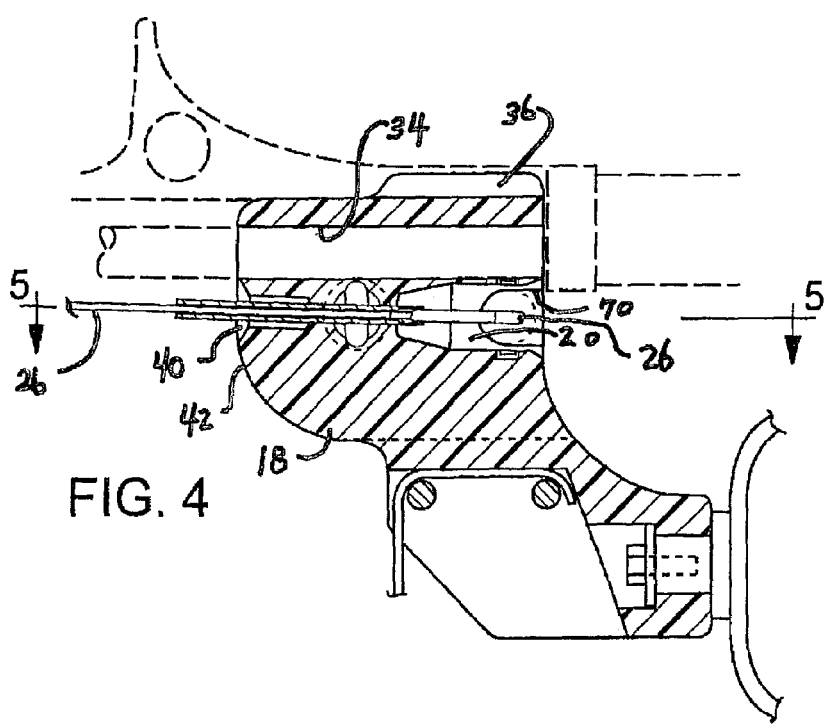
FIG. 4 is a sectional view of the electrosurgical instrument guide block with an electrode shown in place.

The handle section of the working element 10 shown in FIGS. 1–3 generally comprises a frame 12, a handle 14, a thumb guide 16, a guide block 18, and an electrical connector 20 with an integral bipolar power cord 22. Working element 10 also comprises a telescope guide tube 24 and an electrode assembly 26 received in a guide tube 28. Guide tubes 24 and 28 are received in a cooperating sheath (not shown) and extend forward along axis 30 to a working end as is well known in the art. A spring 32 biases guide block 18 in a rearward direction. Guide block 18 includes a telescope guide tube aperture 34 (FIG. 4) through which guide tube 24 extends so that guide block 18 is slidable along guide tube 24 as guide block 18 is moved in a forward direction against spring 32. An anti-rotation guide groove 36 cooperates with frame guide surfaces 38 to prevent rotation of guide block 18.

Thus, guide block 18 is slidably mounted on guide tube 24 and rotationally constrained by frame guide surfaces 38. An electrode reception aperture 40 at a front face 42 of guide block 18 receives a proximal end of electrode assembly 26. An electrode locking mechanism (not shown) cooperates with electrode groove 44 (FIG. 5) to retain the proximal end of electrode assembly 26. A telescope 46 may be inserted into frame 12 that communicates with telescope guide tube 24 whereby telescope 46 can be inserted and retained in working element 10. In operation, an operator grasps handle 14 with fingers and inserts thumb into thumb guide 16 to move guide block 18 in a forward direction compressing spring 32 and axially moving an electrode assembly 26 connected to guide block 18.

Electrical connector 20 is removably inserted into guide block 18 to connect to the proximal end of electrode assembly 26. Once electrical connector 20 is connected to guide block 18 electrosurgical current from an electrosurgical generator (not shown) can be transmitted via power cord 22 and electrical connector 20 directly to electrode assembly 26 to perform a desired operation.

As seen most clearly in FIGS. 1 and 2, electrical connector 20 is connected to guide block 18 through a back face 48. Electrical plug 20 can be connected in alternate first and second positions so that power cord 22 extends from either the left or right side of working element 10 to accommodate right or left-handed users. FIG. 1 shows a view of the handle portion of working element 10 from a position of a user with electrical plug 20 connected to guide block 18 with power cord 22 extending from a user's left side. Alternately, electrical plug 20 can be connected to guide block 18 so that power cord 22 extends from a user's right side as shown in phantom. FIG. 2 shows a front view of the handle portion of working element 10 with electrical plug 20 connected to guide block 18 so that power cord 22 extends from a user's right side. FIG. 2 also shows an alternate position with power cord 22 shown in phantom extending from a user's left side.

By providing a connection at back face 48 of guide block 18 the present invention allows for power cord 22 to be oriented to accommodate different users. For example, a right handed user would generally prefer to have power cord 22 on the left side of guide block 18 so that it would not interfere with the user's movement of guide block 18 or unnecessarily hinder the user's quick and unencumbered access to working element 10 with his or her left hand. Alternatively, a left handed user would prefer to have power cord 22 on the right side of guide block 18 such that the user could operate working element 10 without being annoyed or hindered by the protruding power cord 22.

Figure 5:
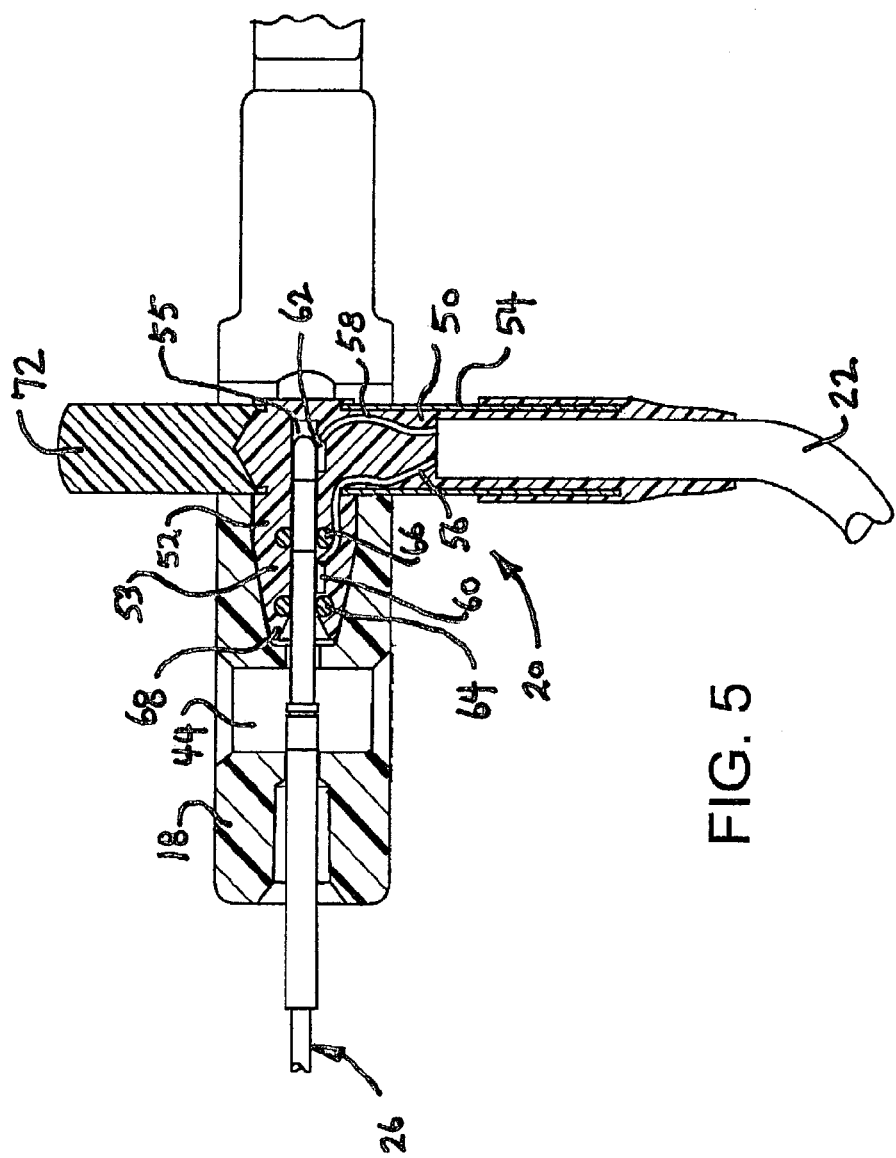
FIG. 5 is a partial sectional top view of the electrical connector positioned in the guide block shown connected to a proximal end of the electrode.
Figure 6:
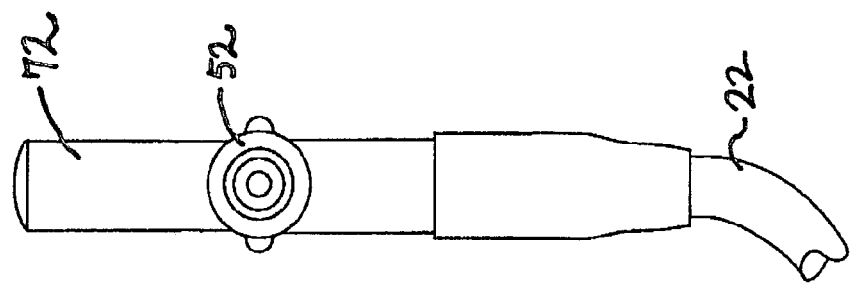
FIG. 6 is side view of the electrical connector.

As best seen in FIG. 5, electrical connector 20 includes a body 50 that is substantially continuous with power cord 22 and an integral plug portion 52 extending substantially perpendicular to body 50. Preferably, body 50 and plug portion 52 are molded as a single unit and made of a nonconductive material which has high lubricity, low moisture absorption, and a good dielectric strength, such as, for example, natural or synthetic rubber or Teflon, a trademark of E.I. Dupont Co. Preferably, plug portion 52 includes a tapered end 53 that mates with and provides a secure connection with guide block 18. Electrical connector 20 is formed integrally with power cord 22 and includes an insulating sheath 54. Plug portion 52 further has a central opening 55 that receives the proximal end of electrode assembly 26 when electrical connector 20 is attached to guide block 18.

Power cord 22 generally includes electrically conductive bipolar wires 56 and 58 that are insulated within power cord 22 which is preferably made of nonconductive elastomeric material such as, for example, silicon rubber. Power cord 22 ends in a standard dual prong plug (not shown) for insertion into an electrical socket located on the electrosurgical power generator. Wire 56 is bonded to a first electrode contact 60 and wire 58 is bonded to outer electrode contact 62. First and second contacts 60 and 62 are made of a conductive material such as, for example, beryllium copper and wires 60 and 62 are bonded to first and second contacts 60 and 62, respectively, preferably by a solder bond. First and second O-rings 64 and 66 are located in central opening 55 to assist holding the proximal end of electrode assembly 26 in plug portion 52 and to seal first and second contacts 60 and 62 from the outside environment. Alternatively, the sealing means can be molded as part of the plug portion 52.

Guide block 18 includes a central opening 68 that is coaxial with electrode reception aperture 40 and, thus, electrode assembly 26. Central opening 68 has a shape that matingly corresponds to plug portion 52 and is in communication with a laterally extending recess 70. Thus, when electrical connector 20 is connected to guide block 18 plug portion 52 is received in opening 68. Body 50 is located within recess 70. A finger-engaging portion 72 (FIG. 5) may be integrally formed on electrical connector 20 to assist in removal of electrical connector 20 from guide block 18.

The present invention generally provides that electrical connector 20 can be connected to guide block 18 at various orientations and positions, but which allows for electrical contact with the electrode assembly 26 which is sealed from the outside environment.

It is important to note that no matter which position or orientation an operator may choose to connect electrical connector 20 to guide block 18, electrical connector 20 will always make electrical contact with the electrode assembly 26.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed:

1. An electrosurgical instrument, comprising:
   an electrode assembly extending along an axis having a working end and a proximal end,
   a guide block mounted on the electrosurgical instrument and connected to the electrode assembly for movement along the axis, the guide block having a first opening through which the proximal end of the electrode assembly extends and a second opening coaxial with the first opening for receiving a portion of an electrical connector to establish electrical contact with the electrode assembly, and
   a removable electrical connector having an integral power cord, the electrical connector having a body that is substantially continuous with the power cord and a plug portion extending substantially transverse to the body, wherein the second opening has a shape that matingly corresponds to the plug portion, so that the plug portion is coaxial with the second opening when the plug portion is inserted into the second opening.

2. The electrosurgical instrument of claim 1, wherein the guide block further comprises a recess for receiving the body of the electrical connector located on a back face thereof extending substantially transverse to the axis and in communication with the second opening.

3. The electrosurgical instrument of claim 1, wherein the plug portion has a central opening for receiving the proximal end of the electrode assembly and plural electrical contacts located within the central opening for establishing electrical communication with the electrode assembly.

4. The electrosurgical instrument of claim 3, wherein the plural electrical contacts include first and second electrical contacts electrically connected to conducting wires of the power cord so that electrical current is transmitted to the electrode assembly when the electrical connector is connected to the guide block.

5. The electrosurgical instrument of claim 4, wherein the plug portion further comprises sealing elements to isolate the first and second electrical contacts.

6. The electrosurgical instrument of claim 1, wherein the electrical connector further comprises a finger-engaging portion to assist in removing the electrical plug from the guide block.

7. The electrosurgical instrument of claim 1, wherein the plug portion is tapered to matingly correspond with the second opening in the guide body.

8. The electrosurgical instrument of claim 1, wherein the electrical connector is made of a non-conductive material.

9. The electrosurgical instrument of claim 8, wherein the electrical connector is made of an elastomeric material.

10. The electrosurgical instrument of claim 1, wherein the electrical connector is adapted to connect to the guide block in multiple positions.

11. The electrosurgical instrument of claim 1, wherein the power cord is bi-polar.

12. An electrosurgical instrument assembly, comprising;
    an electrode assembly extending along an axis having a working end and a proximal end,
    a guide block mounted on the electrosurgical instrument and connected to the electrode assembly for movement along the axis having a first opening coaxial with the electrode assembly, wherein the proximal end of the electrode assembly extends through the first opening, and
    a detachable electrical connector connected to the guide block through a second opening in the guide block that is substantially coaxial with the first opening to establish electrical contact with the electrode assembly, the electrical connector being substantially coaxial with the second opening when received therein.

13. The electrosurgical instrument assembly of claim 12, wherein the guide block and the electrical connector are constructed and arranged so that the electrical connector can be connected to the guide block in plural positions.

14. The electrosurgical instrument assembly of claim 12, wherein the electrical connector is integral with a power cord, the electrical connector further having a body that is substantially continuous with the power cord and a plug portion extending substantially perpendicular to the body.

15. The electrosurgical instrument assembly of claim 13, wherein the electrical connector is adapted to be connected to the guide block to extend from either a first side of the guide block or a second side of the guide block.

16. The electrosurgical instrument assembly of claim 14, wherein the plug portion is received in the second opening in the guide block so that the plug portion is substantially coaxial with the second opening and so that the body extends substantially perpendicular to the guide block.

17. The electrosurgical instrument assembly of claim 12, wherein the guide block includes a front face through which a proximal end of the electrode assembly extends and a back face in which the opening is formed to receive the electrical connector.

18. The electrosurgical instrument assembly of claim 12, wherein the electrical connector is made of a non-conductive material.

19. The electrosurgical instrument assembly of claim 18, wherein the electrical connector is made of an elastomeric material.

20. The electrosurgical instrument assembly of claim 12, wherein the electrical connector forms a sealed connection with the electrode assembly.

21. The electrosurgical Instrument assembly of claim 14, wherein the power cord is bi-polar.

22. An electrosurgical instrument comprising:
a working element having a guide block for receiving a proximal end of an electrical assembly through a first opening in a front face and for receiving an electrical connector through a second opening in a back face to establish an electrical connection with the electrode assembly, the second opening being substantially coaxial with the first opening, so that the electrical connector extends coaxially with the second opening when inserted therein.

23. The electrosurgical instrument of claim 22 further comprising a removable electrical connector having an integral power cord, the electrical connector having a body that is substantially continuous with the power cord and a plug portion extending substantially transverse to the body, so that the plug portion extends substantially coaxially with the second opening when inserted therein.

24. The electrosurgical instrument of claim 23 wherein the second opening in the guide block is constructed and arranged to receive the electrical plug in plural positions to accommodate different users.

25. An electrosurgical instrument assembly, comprising;
a working element having a guide block having a first opening in a front face for receiving a proximal end of an electrical assembly and a second opening in a back face for receiving an electrical connector, the second opening being substantially coaxial with the first opening, and
a detachable electrical connector connected to the guide block through the second opening to establish an electrical connection with the electrode assembly, the second opening being constructed and arranged to receive the electrical connector in plural positions in which the electrical connector is substantially coaxial with the second opening when inserted therein.

26. A method of manufacturing an electrosurgical instrument, comprising the steps of:
providing an electrode assembly extending along an axis having a working end and a proximal end,
providing a guide block mounted on the electrosurgical instrument and connected to the electrode assembly for movement along the axis having a first opening substantially coaxial with the electrode assembly and a second opening substantially coaxial with the first opening, wherein the proximal end of the electrode assembly extends through the first opening, and
providing a detachable electrical connector connected to the guide block through the second opening so that the electrical connector is substantially coaxial with the second opening to establish electrical contact with the electrode assembly.

* * * * *